(12) United States Patent
Shamoto et al.

(10) Patent No.: US 10,768,140 B2
(45) Date of Patent: Sep. 8, 2020

(54) PLATING ANALYSIS METHOD, PLATING ANALYSIS SYSTEM, AND COMPUTER READABLE STORAGE MEDIUM FOR PLATING ANALYSIS

(71) Applicant: EBARA CORPORATION, Tokyo (JP)

(72) Inventors: Mitsuhiro Shamoto, Tokyo (JP); Masashi Shimoyama, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 61 days.

(21) Appl. No.: 16/180,801

(22) Filed: Nov. 5, 2018

(65) Prior Publication Data

US 2019/0137445 A1    May 9, 2019

(30) Foreign Application Priority Data

Nov. 7, 2017 (JP) .................................. 2017-214416

(51) Int. Cl.
| | |
|---|---|
| *G01N 27/42* | (2006.01) |
| *C25D 21/12* | (2006.01) |
| *G01N 33/208* | (2019.01) |
| *G01B 7/06* | (2006.01) |

(52) U.S. Cl.
CPC ............. *G01N 27/42* (2013.01); *C25D 21/12* (2013.01); *G01B 7/06* (2013.01); *G01N 33/208* (2019.01)

(58) Field of Classification Search
CPC ........ G01N 33/208; G01N 27/42; G01B 7/06; C25D 21/12
See application file for complete search history.

(56) References Cited

U.S. PATENT DOCUMENTS

| | | | |
|---|---|---|---|
| 6,542,784 B1 | 4/2003 | Amaya et al. | |
| 2011/0284395 A1* | 11/2011 | Dimitrakopoulos | ... G01N 27/42 |
| | | | 205/789 |
| 2016/0145760 A1 | 5/2016 | Fujikata et al. | |

FOREIGN PATENT DOCUMENTS

| | | |
|---|---|---|
| JP | 2001-152397 A | 6/2001 |
| JP | 2016-098399 A | 5/2016 |

OTHER PUBLICATIONS

Comsol Introduction to Electrodeposition Module version 5.3 (Year: 2017).*

(Continued)

*Primary Examiner* — Alexander S Noguerola
(74) *Attorney, Agent, or Firm* — BakerHostetler (57) ABSTRACT

The present disclosure provides techniques for determining plating conditions by numerically analyzing a film-thickness distribution. The disclosed techniques comprise performing electrochemical measurement in an electroplating apparatus; determining electrochemical parameters based on a result of the electrochemical measurement; receiving initial plating conditions for performing a plating process; based on the electrochemical parameters and the initial plating conditions, determining a current density distribution on a surface of a substrate based on a function formula which comprises a variable which represents a position on the substrate; based on the current density distribution, calculating a thickness of a film to be plated on the substrate; and performing the plating process based on final plating conditions corresponding to a calculated film-thickness distribution satisfying a desired film-thickness distribution.

7 Claims, 3 Drawing Sheets

(56) References Cited

OTHER PUBLICATIONS

COMSOL Release History downloaded from https://www.comsol.com/release-history on Mar. 2, 2020 (Year: 2020).*

Mikael Fredenberg, Electroplating Simulations for Printed Circuit Board Designers, COMSOL Blog, Dec. 17, 2014, downloaded from https://www.comsol.com/blogs/electroplating-simulations-for-printed-circuit-board-designers/ on Feb. 28, 2020 (Year: 2014).*

* cited by examiner

PLATING ANALYSIS METHOD, PLATING ANALYSIS SYSTEM, AND COMPUTER READABLE STORAGE MEDIUM FOR PLATING ANALYSIS

CROSS-REFERENCE TO RELATED APPLICATION

This application is based upon and claims benefit of priority from Japanese Patent Application Nos. 2017-214416 filed on Nov. 7, 2017, the entire contents of which is incorporated herein by reference.

TECHNICAL FIELD

The present invention relates to a method for analyzing plating, a system for analyzing plating, and a computer readable storage medium for analyzing plating.

BACKGROUND ART

Conventionally, a film thickness of a plated film, which is formed by performing an electroplating process, is calculated by performing a simulation based on a numerical analysis method such as a finite element method or the like (for example, refer to Patent Literature 1). By performing simulations, in which conditions with respect to plating are changed in various ways, it becomes possible to derive, in advance, optimum conditions for plating, and apply them to an actual plating process.

When applying electroplating to a substrate which is an object of plating, such as a semiconductor substrate, a printed circuit board, or the like (hereinafter, the "substrate"), an electrically conductive seed layer is formed in advance as a power feed layer on a surface of the substrate, and a plating film is grown on the seed layer. In general, a substrate to be plated has an electric contact on its peripheral part. Thus, current corresponding to combined resistance, which is formed by combining an electric resistance value of a plating solution and an electric resistance value of a part between a center part and the electric contact of the seed layer, flows in the center part of the substrate. On the other hand, current substantially corresponding to the electric resistance value of the plating solution flows in the peripheral part (the part near the electric contact) of the substrate. That is, the flow of the current toward the center part of the substrate is disturbed by the electric resistance between the center part and the electric contact of the seed layer. This phenomenon that the current concentrates around the peripheral part of the substrate is referred to as terminal effect. By the terminal effect, the speed of plating at the center part of the substrate is lowered, so that the film thickness of the plating film at the center part of the substrate becomes thinner than that of the plating film at the peripheral part of the substrate, and, consequently, uniformity in film thickness in a plane is lowered (for example, refer to Patent Literature 2).

CITATION LIST

Patent Literature

PTL 1: Japanese Patent Application Public Disclosure No. 2001-152397
PTL2: Japanese Patent Application Public Disclosure No. 2016-098399

SUMMARY OF INVENTION

Technical Problem

Ununiformity of plated-film thickness in a plane due to terminal effect becomes specially notable in the case that a resist opening ratio of a substrate (the ratio of an area of the regions which are not covered by the resist (the regions of openings of the resist) in the peripheral region to an area of the peripheral region) is small. In other words, uniformity of plated-film thickness in a plane heavily depends on a resist opening ratio of a substrate. Thus, it is important to optimize plating conditions with respect to a pattern substrate which has a resist opening ratio similar to that of an actual product. For realizing the above matter, it may be possible to adopt a method for optimization comprising processes for: applying plating processes under various conditions to plural pattern substrates, wherein a resist has been attached to each of the pattern substrates, and each of the pattern substrates is the same as an actual product; and evaluating thickness of the plated films formed under the respective conditions. However, it requires a high cost to use pattern substrates having resists for finding such conditions. Further, in the example shown in Patent Literature 2, it is necessary to adjust diameters and positions of electric-field adjusting components such as a regulation plate, an anode mask, and so on, so that there is a problem that the work for optimization takes time/labor. Thus, by using numerical-analysis simulation such as that shown in Patent Literature 1, the cost and time required for optimization of plating conditions can be reduced. However, no method for numerically analyzing distribution of plating-film thickness, in which terminal effect is taken into consideration, has been known; and no simulation, from which a result which is highly consistent with distribution of thickness of a plated-film formed on an actual pattern substrate having a resist can be obtained, has been realized.

The present invention has been made by taking the above matters into consideration; and an object of the present invention is to provide a numerical analysis method, by use of which film-thickness distribution of an electroplating film can be calculated.

Solution to Problem

Mode 1

According to Mode 1, a method for analyzing plating is provided, and the method comprises steps for: performing electrochemical measurement in an electroplating apparatus; deriving electrochemical parameters from result of the electrochemical measurement; specifying plating conditions which are applied when performing a plating process; based on the electrochemical parameters and the plating conditions, determining current density distribution on a surface of a substrate which is an object of the plating process, wherein the current density distribution is represented by a predetermined function formula which comprises a variable which represents a position on the substrate; and, based on the current density distribution, calculating thickness of a film plated on the substrate. According to the plating analysis method of Mode 1, the current density on the surface of the substrate is derived, by use of the electrochemical parameters, as a function of a position on the substrate. Thus, the film-thickness distribution of the electroplating film can be obtained in a numerical analysis manner.

Mode 2

According to Mode 2 which comprises the plating analysis method of Mode 1, the predetermined function formula is a function formula which presents small current density in the center part of the substrate, and large current density in the peripheral part of the substrate. The predetermined function formula in Mode 2 reflects position dependence of the current density due to terminal effect. Thus, according to the plating analysis method of Mode 2, ununiformity of plating-film thickness in a plane, which is due to the terminal effect, can be reproduced by use of the numerical analysis.

Mode 3

According to Mode 3 which comprises the plating analysis method of Mode 1 or Mode 2, the step for determining current density distribution comprises a step for determining a variable of the predetermined function formula, based at least on the electrochemical parameters. According to the plating analysis method of Mode 3, current density distribution on the surface of the substrate can be determined, by determining, based on the electrochemical parameters, a variable of the predetermined function formula.

Mode 4

According to Mode 4 which comprises one of the plating analysis methods of Mode 1 to Mode 3, the electrochemical parameters comprise polarization resistance, exchange current density, and equilibrium potential. According to the plating analysis methods of Mode 4, the predetermined function formula can be determined by using polarization resistance, exchange current density, and equilibrium potential obtained from the electrochemical measurement.

Mode 5

According to Mode 5, a system for analyzing plating, which comprises an electroplating apparatus and a computer, is provided, wherein: the computer is constructed to derive electrochemical parameters from result of electrochemical measurement in the electroplating apparatus; specify plating conditions which are applied when performing a plating process; based on the electrochemical parameters and the plating conditions, determine current density distribution on a surface of a substrate, which is an object of the plating process, as a predetermined function formula which comprises a variable which represents a position on the substrate; and, based on the current density distribution, calculate thickness of a film plated on the substrate. According to the plating analysis system of Mode 5, the current density on the surface of the substrate is derived, by use of the electrochemical parameters, as a function of a position on the substrate. Thus, the film-thickness distribution of the electroplating film can be obtained in a numerical analysis manner.

Mode 6

According to Mode 6 which comprises the plating analysis system of Mode 5, the position of the electroplating apparatus and the position of the computer are distant from each other, and the electroplating apparatus and the computer are connected to each other via a communication means to be able to communicate to/from one another. According to the plating analysis system of Mode 6, analysis of plating-film thickness can be performed at a location, which is distant from that of the electroplating apparatus, by use of the computer.

Mode 7

According to Mode 7, a computer readable storage medium storing thereon computer executable instructions for analyzing plating is provided, and the computer executable instructions, when executed by a processor of a computer, cause the processor to perform steps for: deriving electrochemical parameters from result of electrochemical measurement in an electroplating apparatus; specifying plating conditions which are applied when performing a plating process; based on the electrochemical parameters and the plating conditions, determining current density distribution on a surface of a substrate, which is an object of the plating process, as a predetermined function formula which comprises a variable which represents a position on the substrate; and, based on the current density distribution, calculating thickness of a plating film on the substrate. According to the computer readable storage medium for plating analysis of Mode 7, the current density on the surface of the substrate is derived, by use of the electrochemical parameters, as a function of a position on the substrate. Thus, the film-thickness distribution of the electroplating film can be obtained in a numerical analysis manner.

DESCRIPTION OF EMBODIMENTS

An embodiment of the present invention will be explained with reference to the figures. In the figures, the same or similar reference symbols are assigned to the same or similar components; and, in the explanations of respective embodiments, duplicated explanations with respect to the same or similar components will be omitted. Further, the characteristic constructions shown in the embodiments are applicable to other embodiments if they are not contradictory to each other.

Figure 1:
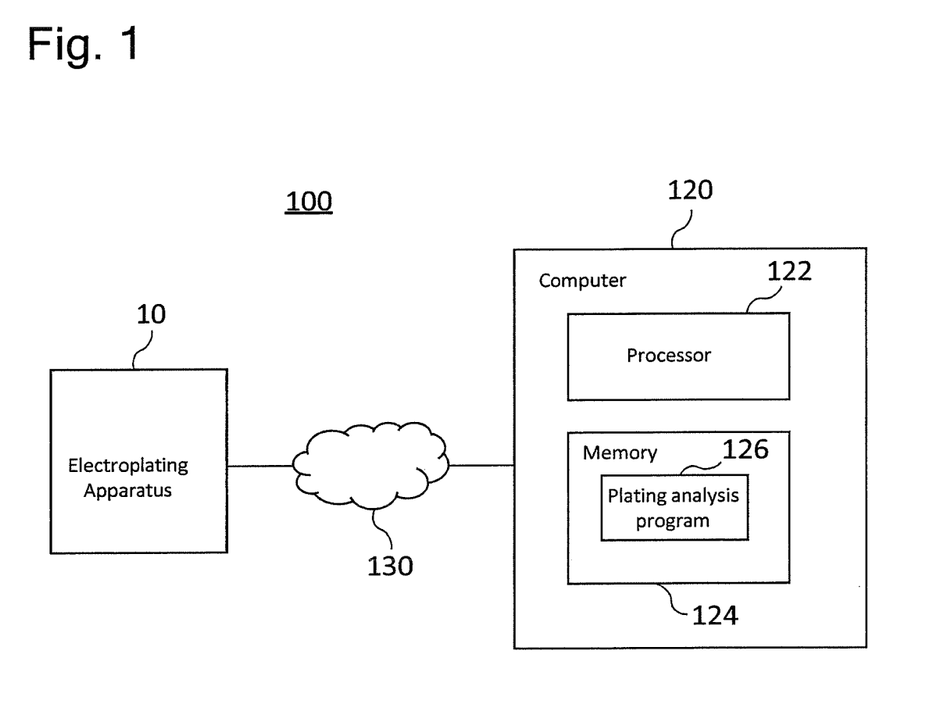
FIG. 1 is a block diagram of a plating analysis system according to an embodiment of the present invention.

FIG. 1 is a block diagram of a plating analysis system 100 according to an embodiment of the present invention. The plating analysis system 100 comprises an electroplating apparatus 10 and a computer 120. The position of the electroplating apparatus 10 and the position of the computer 120 are distant from each other, and the electroplating apparatus 10 and the computer 120 are connected to each other via a network (a communication means) 130, such as a LAN (local area network), a WAN (wide area network), the Internet, or the like, to be able to communicate to/from one another. In this regard, note that the electroplating apparatus 10 and the computer 120 may be positioned at a same place, and connected to each other. Alternatively, a plating analysis program 126, which will be explained later, may be installed on the electroplating apparatus 10.

Figure 2:
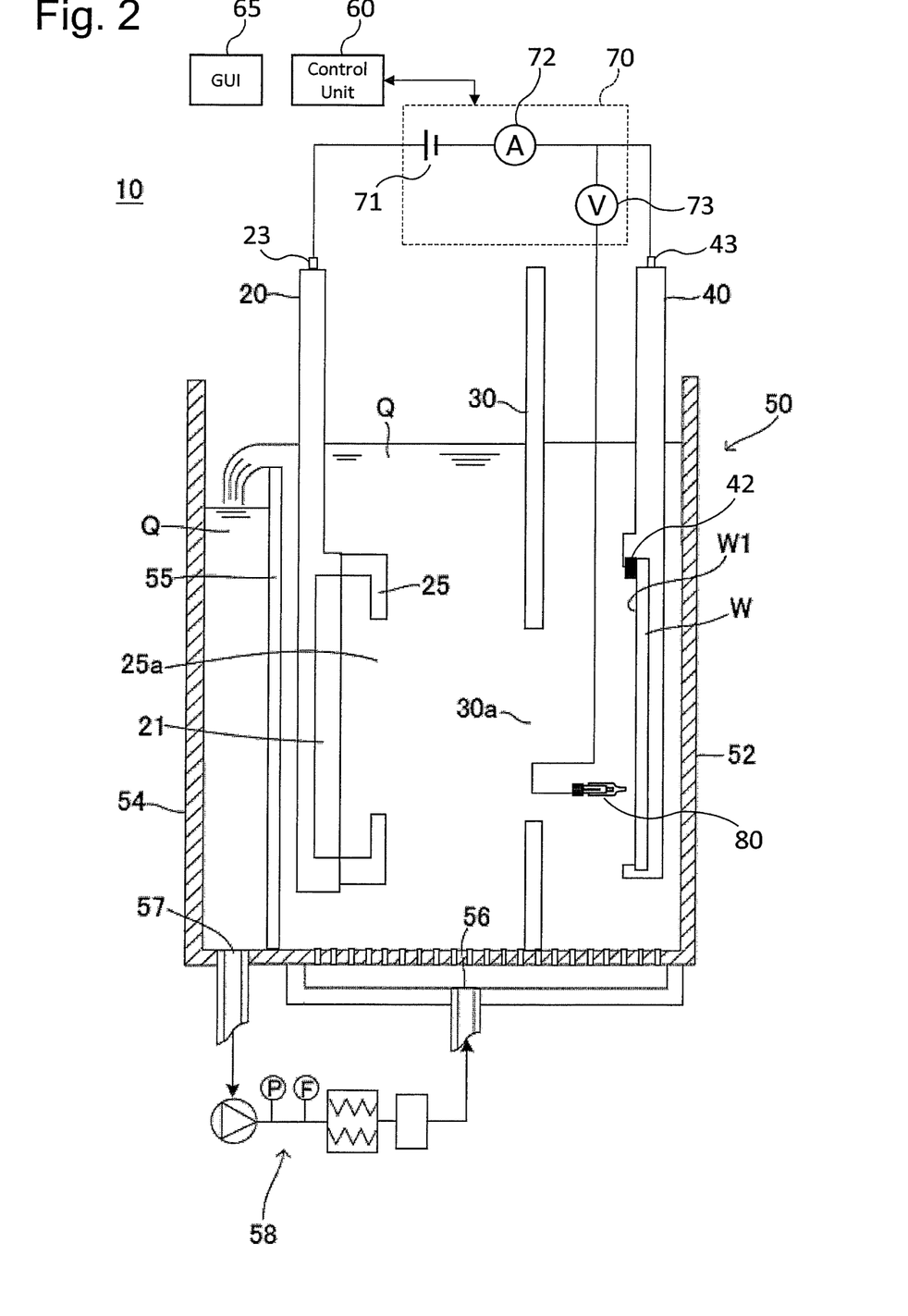
FIG. 2 is a schematic cross-section view of an electroplating apparatus.

FIG. 2 is a schematic cross-section view of the electroplating apparatus 10. As shown in the figure, the electroplating apparatus 10 comprises an anode holder 20 which is constructed to hold an anode 21, a substrate holder 40 which is constructed to hold a substrate W, and a plating tank 50 which houses the anode holder 20 and the substrate holder 40. The electroplating apparatus 10 also comprises a control unit 60 for controlling a plating process and electrochemical measurement performed in the electroplating apparatus 10. Further, electroplating apparatus 10 comprises a display part and a user input/output part for providing a GUI (graphical user interface) to/from which various types of data can be inputted/outputted.

The anode 21 is electrically connected to a potentiostat 70 via an electric terminal 23 on the anode holder 20. The substrate W is electrically connected to the potentiostat 70, via an electric terminal 42 which is in contact with a peripheral part of the substrate W, and an electric terminal 43 on the substrate holder 40. The potentiostat 70 comprises a DC power source 71, a current measuring circuit 72, and an electric potential measuring circuit 73. The DC power source 71 supplies current which flows between the anode 21 and the substrate W. The current measuring circuit 72 measures current which flows between the anode 21 and the substrate W. A reference electrode 80, which is electrically connected to the electric potential measuring circuit 73, is arranged at a position near a surface W1, which is to be plated, of the substrate W. The electric potential measuring circuit 73 measures, based on an electric potential of the reference electrode 80, an electric potential of the to-be-plated surface W1 of the substrate W (an electric potential difference between the electric potential of the reference electrode 80 and that of the to-be-plated surface W1 of the substrate W).

The anode holder 20 holding the anode 21 and the substrate holder 40 holding the substrate W are soaked in a plating solution Q in a plating treatment tank 52, and are arranged to face each other so as to arrange the anode 21 and the to-be-plated surface W1 of the substrate W to be approximately in parallel with each other. Under the state that the anode 21 and the substrate W are soaked in the plating solution Q in the plating treatment tank 52, a voltage is applied from the DC electric source 71 to the anode 21 and the substrate W. As a result thereof, reduction of metal ions occurs at the to-be-plated surface W1 of the substrate W, and a film is formed on the to-be-plated surface W1.

The anode holder 20 comprises an anode mask 25 for adjusting an electric field between the anode 21 and the substrate W. The anode mask 25 is, for example, a member which is approximately flat and comprises dielectric material, and formed on a front surface of the anode holder 20. In this regard, the front surface of the anode 20 is that facing the substrate holder 40. That is, the anode mask 25 is arranged at a position between the anode 21 and the substrate holder 40. The anode mask 25 comprises, approximately at its center part, a first opening 25a through which current flowing between the anode 21 and the substrate W passes. It is preferable that the diameter of the first opening 25a is smaller than that of the anode 21. The anode mask 25 may be constructed in such a manner that the diameter of the first opening 25a is adjustable.

The electroplating apparatus 10 further comprises a regulation plate 30 for adjusting the electric field between the anode 12 and the substrate W. The regulation plate 30 is, for example, a member which is approximately flat and comprises dielectric material, and arranged between the anode mask 25 and the substrate holder 40 (the substrate W). The regulation plate 30 comprises a second opening 30a through which current flowing between the anode 21 and the substrate W passes. It is preferable that the diameter of the second opening 30a is smaller than that of the substrate W. The regulation plate 30 may be constructed in such a manner that the diameter of the second opening 30a is adjustable.

As shown in FIG. 2, the plating tank 50 comprises the plating treatment tank 52 for holding a plating solution Q including additives, a plating solution discharge tank 54 for receiving and discharging the plating solution Q overflowed from the plating treatment tank 52, and a partition wall 55 for separating the plating treatment tank 52 and the plating solution discharge tank 54.

The plating treatment tank 52 comprises a plating solution inlet 56 for supplying the plating solution Q to the inside of the tank. The plating solution discharge tank 54 comprises a plating solution outlet 57 for discharging the plating solution Q overflowed from the plating treatment tank 52. The plating solution inlet 56 is positioned at a bottom part of the plating treatment tank 52, and the plating solution outlet 57 is positioned at a bottom part of the plating solution discharge tank 54.

The plating solution Q, when supplied from the plating solution inlet 56 to the plating treatment tank 52, overflows the plating treatment tank 52, thus, flows over the partition wall 55 and into the plating solution discharge tank 54. The plating solution Q flown into the plating solution discharge tank 54 is discharged from the plating solution outlet 57, and impurities or the like in the discharged plating solution Q are removed by a filter and so on in a plating solution circulation device 58. The plating solution Q, from which the impurities were removed, is supplied to the plating treatment tank 52 by the plating solution circulation device 58 via the plating solution inlet 56.

Referring to FIG. 1 again, the computer 120 of the plating analysis system 100 comprises a processor 122 and a memory 124. The memory 124 stores a plating analysis program 126 for realizing a plating analysis method according to the embodiment of the present invention. The processor 122 reads the plating analysis program 126 out of the memory 124 and executes it.

Figure 3:
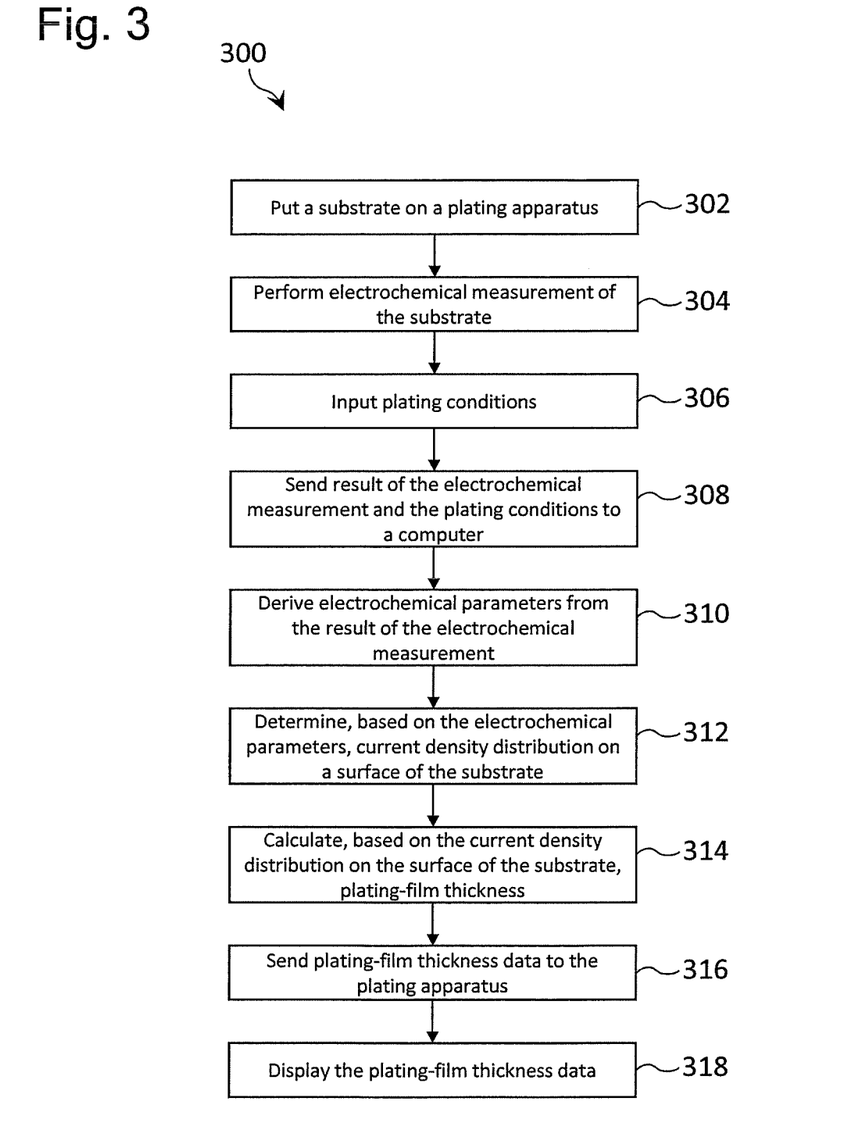
FIG. 3 is a flow chart showing a plating analysis method according to an embodiment of the present invention.

FIG. 3 is a flow chart showing a plating analysis method 300 according to an embodiment of the present invention.

First, in step 302, the substrate W is put on the substrate holder 40 of the electroplating apparatus 10. For example, the substrate W may be a pattern substrate to which a resist has been added, wherein a resist film is formed on regions except for those on which patterns, such as a fine wiring pattern and so on, are to be formed by applying a plating process. In other words, in this example, the substrate W comprises a resist film on its surface, and the resist film comprises resist openings having shapes corresponding to patterns, such as a fine wiring pattern and so on, which are to be formed by applying a plating process. As previously explained, in a substrate such as the substrate W, terminal effect may occur notably.

Next, in step 304, electrochemical measurement with respect to the substrate W is performed by use of the electroplating apparatus 10. The electrochemical measurement with respect to the substrate W is performed by controlling the potentiostat 70 by the control unit 60 of the electroplating apparatus 10. Specifically, the control unit 60 controls an output voltage from the DC electric source 71 (the voltage across the anode 21 and the substrate W), to make the electric potential of the to-be-plated surface W1 of the substrate W, which is to be measured by the electric potential measuring circuit 73 of the potentiostat 70, to have a predetermined constant value. As a result thereof, reduction of metal ions occurs at the to-be-plated surface W1 of the substrate W, and, in association therewith, electron moves between the anode 21 and the substrate W, i.e., current is generated therebetween. The control unit 60 then records a combination of the current value measured at that time by the current measuring circuit 72 of the potentiostat 70 and the electric potential of the to-be-plated surface W1 of the substrate W which is controlled to have a constant value (the electric potential measured by the electric potential measuring circuit 73). The control unit 60 repeatedly performs measurement for obtaining combinations of such electric potential and current, while changing the electric potential of the to-be-plated surface W1 of the substrate W in various ways. Based on the result thereof, a polarization curve (a current-potential curve) representing relationship between the electric potential of the to-be-plated surface W1 of the substrate W and the current flowing between the anode 21 and the substrate W is obtained.

Next, in step 306, predetermined plating conditions, which are used in a numerical analysis which will be explained later, is inputted by a user via the GUI 165 of the electroplating apparatus 10. The predetermined plating conditions include current density which is calculated by dividing the value of the current flowing between the anode 21 and the substrate W by the area of the openings of the resist on the substrate W, temperature of the plating solution Q, the length of time that the plating process is performed (plating thickness desired to be obtained), the diameter of the first opening 25a of the anode mask 25, the diameter of the second opening 30a of the regulation plate 30, distance between electrodes (i.e., the distance between the anode 21 and the substrate W), film thickness of the seed layer formed on the to-be-plated surface W1 of the substrate W, length of the tunnel of the regulation plate 30 (the depth of the second opening 30a), distance between the substrate W and the regulation plate 30, and so on. In the predetermined conditions, the temperature of the plating solution Q, the distance between electrodes, and the film thickness of the seed layer are parameters which affect the polarization curve; thus, it is desirable to use the conditions at the time that the electrochemical measurement with respect to the substrate W is performed in step 304.

Next, in step 308, the result of electrochemical measurement performed with respect to the substrate W (data of the polarization curve) and the plating conditions inputted by the user are sent from the electroplating apparatus 10 to the computer 120.

Next, in step 310, by executing the plating analysis program 126 in the computer 120, electrochemical parameters are derived from the result of electrochemical measurement with respect to the substrate W. The electrochemical parameters include polarization resistance (Tafel slope), exchange current density, and equilibrium potential. Each of these parameters can be obtained from the Tafel plot of the polarization curve obtained from the electrochemical measurement. In this regard, it is possible to adopt a construction that the electrochemical parameters are derived by the control unit 60 of the electroplating apparatus 10, and the derived electrochemical parameters are sent from the electroplating apparatus 10 to the computer 120.

Next, in step 312, by executing the plating analysis program 126, current density distribution on the surface of the substrate W is determined based on the above electrochemical parameters. The determined current density distribution is that reflecting the predetermined plating conditions inputted to the electroplating apparatus 10 in step 306. The current density distribution on the surface of the substrate W is represented by a predetermined function formula which has position dependence which simulates terminal effect. By calculating, based on the above electrochemical parameters, respective coefficients of the function formula, the current density distribution on the surface of the substrate W is determined.

For example, current density $I_p(r)$ and overcurrent $\eta_p(r)$ at position r on the substrate W may be represented by the formulas shown below. In this regard, note that the position r on the substrate W is represented by r=x/L, wherein x is the distance from the center of the substrate W to the position r, and L is the distance between the electric contact 42 of the substrate W and the center of the substrate W.

$$I_p(r) = \kappa \frac{I_0}{(r_t^2 - r^2)\frac{\xi}{4} + \exp(-\phi_{t2})} \quad (1)$$

$$\eta_p(r) = \frac{-\ln\left[(r_c^2 - r^2)\frac{\xi}{4} + \exp(\phi_{t2})\right]}{b} \quad (2)$$

In this case, a dimensionless polarization parameter $\xi$ a current displacement point $r_t$, and an overvoltage norm $\varphi_{t2}$ at the current displacement point $r_t$ are defined by the formulas shown below, respectively.

$$\xi = bR_s I_0 L^2 \quad (3)$$

$$r_t = \frac{10C\sqrt{\frac{\xi}{2}} - \sqrt{10\xi C^2}}{4\xi} \quad (4)$$

$$C = \sqrt{\frac{\xi}{2} + \exp\left(-\frac{b\eta_0}{2}\right)} \quad (5)$$

$$\phi_{t2} = -2\ln\left[(1-r_t)\sqrt{\frac{\xi}{2}} + \exp\left\{-\frac{b(\phi_2 - \phi_1 - E_{eq})}{2}\right\}\right] \quad (6)$$

Regarding the above formulas, definitions of the respective variables therein are as follows: $I_0$ denotes exchange current density, b denotes polarization resistance, $\eta_0$ denotes overvoltage relating to applied current flowing between the anode 21 and the substrate W, $\varphi_S$ denotes electric potential of the substrate W, $\varphi_1$ denotes electric potential in the plating solution Q, $E_{eq}$ denotes equilibrium potential, and $R_S$ denotes surface resistance of the seed layer of the substrate W. Further, $\kappa$ denotes an optional correction factor. These variables are obtained from the result of electrochemical measurement with respect to the substrate W, or other measurement or analysis.

As shown by formula (1), the current density $I_p(r)$ becomes smaller as the position approaches closer to the center part of the substrate W, and becomes larger as the position approaches closer to the peripheral part of the substrate W. Thus, the current density distribution on the surface of the substrate W, which is represented by using the current density $I_p(r)$ of formula (1), reflects position dependence of the terminal effect.

Next, in step 314, by executing the plating analysis program 126, film thickness of a plating film plated on the substrate W is calculated, based on the current density distribution on the surface of the substrate W which is determined as described above. For example, the film thickness Th(r) of the plating film may be calculated by using the current density $I_p(r)$ and according to the following formula. In this regard, note that Mw denotes atomic weight of a metal used for plating, t denotes the length of time that the plating process is performed, ρ denotes density of the metal used for plating, n denotes the number of reaction electrons, and F denotes the Faraday constant.

$$Th(r) = \frac{Mw \times I_p(r) \times l}{\rho \times n \times P} \tag{7}$$

In this manner, the film-thickness distribution of the plating film, which reflects the terminal effect, can be obtained by numerical analysis.

Next, in step 316, data of the above calculated film thickness Th(r) of the plating film are sent from the computer 120 to the electroplating apparatus 10.

Next, in step 318, the data of the film thickness Th(r), which are result of the numerical analysis, are displayed on the GUI 165 of the electroplating apparatus 10. The user confirms the data of the film thickness Th(r), and may repeat step 306 and steps after step 306, as necessary, for performing recalculation of film thickness of the plating film by using new different plating conditions. Recalculation of film thickness may be repeated for an arbitrary number of times, i.e., until desired film-thickness distribution is obtained. As a result thereof, the user can obtain final plating conditions which are required for realizing the desired film-thickness distribution.

By using the plating analysis system 100 according to the embodiment, analysis of film thickness may be performed by use of the computer 120 at a location distant from that of the electroplating apparatus 10. It is not required to install the plating analysis program 126 in the electroplating apparatus 10, and it is also possible to perform plating-film thickness analyses for plural pieces of electroplating apparatus 10, respectively, by use of a single computer 120. Work for setting different plating conditions for obtaining desired film-thickness distribution may be performed by an operator who manipulates the electroplating apparatus 10 or an operator who manipulates the computer 120.

According to the plating analysis method according to the embodiment, electrochemical measurement with respect to a substrate, which is the object for which optimization of plating-film thickness distribution is to be attempted, is first performed. Thus, a polarization curve (a current-potential curve), which reflects characteristics of the substrate such as a resist opening ratio and so on and is peculiar to the substrate, is obtained. Accordingly, accurate plating-film thickness distribution can be obtained by performing analysis.

In the above description, embodiments of the present invention are explained based on some examples; and the above embodiments of the present invention are those used for facilitating understanding of the present invention, and are not those for limiting the present invention. It is obvious that the present invention can be changed or modified without departing from the scope of the gist thereof, and that the scope of the present invention includes equivalents thereof. Further, it is possible to arbitrarily combine components or omit a component (components) disclosed in the claims and the specification, when covering the scope that at least part of the above-stated problems can be solved, and/or the scope that at least part of advantageous effect can be obtained.

REFERENCE SIGNS LIST

10 Electroplating apparatus
20 Anode holder
21 Anode
23 Electric terminal
25 Anode mask
25a First opening
30 Regulation plate
30a Second opening
40 Substrate holder
42 Electric contact
43 Electric terminal
50 Plating tank
52 Plating treatment tank
54 Plating solution discharge tank
55 Partition wall
56 Plating solution inlet
57 Plating solution outlet
58 Plating solution circulation device
60 Control unit
65 GUI
70 Potentiostat
71 DC power source
72 Current measuring circuit
73 Electric potential measuring circuit
80 Reference electrode
100 Plating analysis system
120 Computer
122 Processor
124 Memory
126 Plating analysis program
130 Network
Q Plating solution
W Substrate
W1 Surface to be plated

What is claimed is:

1. A method for determining plating conditions by numerically analyzing a film-thickness distribution, comprising:
   performing an electrochemical measurement in an electroplating apparatus;
   determining electrochemical parameters based on a result of the electrochemical measurement;
   receiving plating conditions for performing a plating process;
   based on the electrochemical parameters and the plating conditions, determining a current density distribution on a surface of a substrate which is an object of the plating process, wherein the current density distribution is determined based on a function formula which comprises a variable which represents a position on the substrate; based on the current density distribution, calculating a thickness distribution of a film to be on the substrate,
   wherein the predetermined function formula is given as $$I_P(r) = \kappa \frac{I_0}{(r_t^2 - r^2)\frac{\xi}{4} + \exp(-\phi_{t2})}, \tag{1}$$

wherein $I_p(r)$ denotes the current density distribution at position r on the substrate, wherein a dimensionless polarization parameter ξ, a current displacement point $r_t$, and an overvoltage norm $\varphi_{t2}$ at the current displacement point $r_t$ are given respectively as $$\xi = bR_s I_0 L^2, \quad (3)$$

$$r_t = \frac{10C\sqrt{\frac{\xi}{2}} - \sqrt{10\xi C^2}}{4\xi}, \quad (4)$$

$$C = \sqrt{\frac{\xi}{2}} + \exp\left(-\frac{b\eta_0}{2}\right), \text{ and} \quad (5)$$

$$\phi_{t2} = -2\ln\left[(1-r_t)\sqrt{\frac{\xi}{2}} + \exp\left\{-\frac{b(\phi_z - \phi_l - E_{eq})}{2}\right\}\right], \quad (6)$$

wherein $I_0$ denotes exchange current density, b denotes polarization resistance, $\eta_0$ denotes overvoltage relating to applied current, $\varphi_S$ denotes electric potential of the substrate, $\varphi_1$ denotes electric potential in a plating solution, $E_{eq}$ denotes equilibrium potential, $R_S$ denotes surface resistance of a seed layer of the substrate, κ denotes an optional correction factor, and L denotes the distance between an electric contact of the substrate and the center of the substrate; and performing the plating process based on plating conditions corresponding to a calculated film-thickness distribution satisfying a desired film-thickness distribution.

2. The method according to claim 1, wherein the function formula is a function formula which presents small current density in the center part of the substrate, and large current density in the peripheral part of the substrate.

3. The method according to claim 1, wherein the determining a current density distribution comprises determining variables of the function formula based at least on the electrochemical parameters.

4. The method according to claim 1, wherein the electrochemical parameters comprise the polarization resistance, the exchange current density, and the equilibrium potential.

5. A system for determining plating conditions, comprising:
an electroplating apparatus; and
a computer communicatively coupled to the electroplating apparatus and configured to at least perform operations comprising:
determine electrochemical parameters based on a result of an electrochemical measurement received from the electroplating apparatus,
receive plating conditions to be applied by the electroplating apparatus when performing a plating process,
based on the electrochemical parameters and the plating conditions, determine a current density distribution on a surface of a substrate, which is an object of the plating process, based on a function formula which comprises a variable which represents a position on the substrate,
based on the current density distribution, calculate a thickness distribution of a film to be plated on the substrate by the electroplating apparatus,
wherein the predetermined function formula is given as $$I_P(r) = \kappa \frac{I_0}{(r_t^2 - r^2)\frac{\xi}{4} + \exp(-\phi_{t2})}, \quad (1)$$

wherein $I_p(r)$ denotes the current density distribution at position r on the substrate, wherein a dimensionless polarization parameter ξ, a current displacement point $r_t$, and an overvoltage norm $\varphi_{t2}$ at the current displacement point $r_t$ are given respectively as $$\xi = bR_s I_0 L^2, \quad (3)$$

$$r_t = \frac{10C\sqrt{\frac{\xi}{2}} - \sqrt{10\xi C^2}}{4\xi}, \quad (4)$$

$$C = \sqrt{\frac{\xi}{2}} + \exp\left(-\frac{b\eta_0}{2}\right), \text{ and} \quad (5)$$

$$\phi_{t2} = -2\ln\left[(1-r_t)\sqrt{\frac{\xi}{2}} + \exp\left\{-\frac{b(\phi_z - \phi_l - E_{eq})}{2}\right\}\right], \quad (6)$$

wherein $I_0$ denotes exchange current density, b denotes polarization resistance, $\eta_0$ denotes overvoltage relating to applied current, $\varphi_S$ denotes electric potential of the substrate, $\varphi_1$ denotes electric potential in a plating solution, $E_{eq}$ denotes equilibrium potential, $R_S$ denotes surface resistance of a seed layer of the substrate, κ denotes an optional correction factor, and L denotes the distance between an electric contact of the substrate and the center of the substrate, and storing final plating conditions for performing the plating process, the final plating conditions corresponding to plating conditions applied in calculating the thickness distribution where the thickness distribution satisfies a desired thickness distribution.

6. The system according to claim 5, wherein a position of the electroplating apparatus and a position of the computer are distant from each other, and the electroplating apparatus and the computer are connected to each other via a communication means to be able to communicate to and from one another.

7. A computer readable storage medium storing thereon computer executable instructions for determining plating conditions by numerically analyzing a film-thickness distribution, wherein the computer executable instructions, when executed by a processor of a computer, cause the processor to:
determine electrochemical parameters based on a result of an electrochemical measurement received from an electroplating apparatus;
receive plating conditions to be applied by the electroplating apparatus when performing a plating process;
based on the electrochemical parameters and the plating conditions, determine a current density distribution on a surface of a substrate, which is an object of the plating process, based on a function formula which comprises a variable which represents a position on the substrate;
based on the current density distribution, calculate a thickness distribution of a film to be plated on the substrate,
wherein the predetermined function formula is given as $$I_P(r) = \kappa \frac{I_0}{(r_t^2 - r^2)\frac{\xi}{4} + \exp(-\phi_{t2})}, \quad (1)$$

wherein $I_p(r)$ denotes the current density distribution at position r on the substrate, wherein a dimensionless polarization parameter $\xi$, a current displacement point $r_t$, and an overvoltage norm $\varphi_{t2}$ at the current displacement point $r_t$ are given respectively as $$\xi = bR_s I_0 L^2, \qquad (3)$$

$$r_t = \frac{10C\sqrt{\frac{\xi}{2}} - \sqrt{10\xi C^2}}{4\xi}, \qquad (4)$$

$$C = \sqrt{\frac{\xi}{2}} + \exp\left(-\frac{b\eta_0}{2}\right), \text{ and} \qquad (5)$$

$$\phi_{t2} = -2\ln\left[(1-r_t)\sqrt{\frac{\xi}{2}} + \exp\left\{-\frac{b(\phi_z - \phi_l - E_{eq})}{2}\right\}\right], \qquad (6)$$

wherein $I_0$ denotes exchange current density, b denotes polarization resistance, $\eta_0$ denotes overvoltage relating to applied current, $\varphi_S$ denotes electric potential of the substrate, $\varphi_1$ denotes electric potential in a plating solution, $E_{eq}$ denotes equilibrium potential, $R_S$ denotes surface resistance of a seed layer of the substrate, κ denotes an optional correction factor, and L denotes the distance between an electric contact of the substrate and the center of the substrate; and storing final plating conditions for performing the plating process, the final plating conditions corresponding to plating conditions applied in calculating the thickness distribution where the thickness distribution satisfies a desired thickness distribution.

* * * * *